(12) United States Patent
Vilsmeier

(10) Patent No.: US 9,911,199 B2
(45) Date of Patent: Mar. 6, 2018

(54) USING DIFFERENT INDICATORS FOR DETERMINING POSITIONAL CHANGES OF A RADIOTHERAPY TARGET

(75) Inventor: Stefan Vilsmeier, Munich (DE)

(73) Assignee: Brainlab AG, Munich (DE)

( * ) Notice: Subject to any disclaimer, the term of this patent is extended or adjusted under 35 U.S.C. 154(b) by 608 days.

(21) Appl. No.: 14/383,121

(22) PCT Filed: Mar. 5, 2012

(86) PCT No.: PCT/EP2012/053718
§ 371 (c)(1),
(2), (4) Date: Sep. 5, 2014

(87) PCT Pub. No.: WO2013/131547
PCT Pub. Date: Sep. 12, 2013

(65) Prior Publication Data
US 2015/0038765 A1    Feb. 5, 2015

(51) Int. Cl.
*A61N 5/00* (2006.01)
*G06T 7/246* (2017.01)
(Continued)

(52) U.S. Cl.
CPC ............ *G06T 7/246* (2017.01); *A61B 6/5217* (2013.01); *A61N 5/1049* (2013.01); *A61B 6/032* (2013.01);
(Continued)

(58) Field of Classification Search
CPC .... A61N 5/103; A61N 5/1037; A61N 5/1039; A61N 5/1083; A61N 5/1084; A61N 5/1049; A61N 5/1064; A61N 5/1067
(Continued)

(56) References Cited

U.S. PATENT DOCUMENTS

| | | | |
|---|---|---|---|
| 7,922,391 B2 | 4/2011 | Essenreiter et al. | |
| 2010/0125195 A1 | 5/2010 | Berlinger et al. | |

(Continued)

FOREIGN PATENT DOCUMENTS

| | | |
|---|---|---|
| EP | 2189940 | 5/2010 |
| EP | 2189943 | 5/2010 |
| WO | 2011107145 | 9/2011 |

OTHER PUBLICATIONS

Lin et al., "Tumor Targeting for Lung Cancer Radiotherapy Using Machine Learning Techniques", Machine Learning and Applications, 2008, pp. 533-538.
(Continued)

*Primary Examiner* — John Lacyk
(74) *Attorney, Agent, or Firm* — Tucker Ellis LLP

(57) ABSTRACT

The present invention relates to a method for determining data referred to as target change data which can be used for performing radiotherapy treatment, the target change data describing information on the change of position of a target included in a body of a patient, the method being performed by a computer and comprising the following steps:
 acquiring determination rule data describing a rule for mapping an indicator change set to the target change data, the indicator change set being a set which comprises more than one element, the elements of the indicator change set respectively representing information on respective changes of positions of indicators, at least two of the indicators respectively indicating a change of position of different body structures referred to as indicator structures,
 acquiring set data describing an acquired indicator change set; and
 determining the target change data based on the determination rule data and the set data by applying the rule for mapping to the acquired indicator change set.

15 Claims, 4 Drawing Sheets

(51) Int. Cl.
    *A61B 6/00*     (2006.01)
    *A61N 5/10*     (2006.01)
    *A61B 6/03*     (2006.01)
    *G06K 9/32*     (2006.01)
    *A61B 34/20*     (2016.01)

(52) U.S. Cl.
    CPC .............. *A61B 34/20* (2016.02); *A61N 5/1064* (2013.01); *G06K 2009/3225* (2013.01); *G06T 2207/30096* (2013.01)

(58) Field of Classification Search
    USPC ........................................................ 600/1–8
    See application file for complete search history.

(56) References Cited

U.S. PATENT DOCUMENTS

| | | |
|---|---|---|
| 2010/0160836 A1 | 6/2010 | Berlinger |
| 2012/0004518 A1 | 1/2012 | Souza et al. |

OTHER PUBLICATIONS

Xing et al., Overview of Image-Guided Radiation Therapy, Medical Dosimetry, vol. 31, No. 2, May 2006, pp. 91-112.

Schreibmann, Ph.D., et al., "Image Interpolation in 4D CT Using a Bspline Deformable Registration Model", International Journal of Radiation: Oncology Biology Physics, vol. 64, No. 5, Apr. 2006, pp. 1537-1550.

Schweikard et al., "Fiducial-Less Respiration Tracking in Radiosurgery", Lecture Notes in Computer Science/Computational Science, vol. 3217, No. 1, Jan. 2004, pp. 992-999.

Schweikard et al., "Robotic Motion Compensation for Respiratory Movement during Radiosurgery", Computer Aided Surgery, vol. 5, No. 4, Jan. 2000, pp. 263-277.

International Search Report and Written Opinion for International Application No. PCT/EP2012/053718 dated Nov. 22, 2012.

Ross et al., Real-Time Liver Motion Compensation for MRgFUS, Medical Image Computing and Assisted Intervention MICCAI 2008, Springer-Verlag Berlin Heidelberg, pp. 806-813, XP19105238, ISBN: 85989-5, USA.

Villard et al., Modelling Organ Deformation Using Mass-Springs and Tensional Integrity, Biosurgery and Surgical Technology Department, Imperial College London,ISBMS 2008, LNCS 5104, pp. 221-226, Jul. 7-8, 2008, London, UK.

Yaniv et al., Fluoroscopic Image Processing for Computer-Aided Orthopedic Surgery, MICCAI,1998, Lecture Notes in Computer Science, vol. 1496, Springer, Berlin, Heidelberg, pp. 325-334, USA.

Tsai et al., An Efficient an Accurate Camera Calibration Technique for 3D Machine Vision, Proceedings of the IEEE Conference on Computer Vision and Recognition, Miami Beach, Florida, 1986, pp. 364-374.

Tasi et al., A Versatile Camera Calibration Technique for High-Accuracy 3D Machine Vision Metrology Using Off-the-Shelf TV Cameras and Lenses, IEEE Journal of Robotics and Automation, vol. RA-3, No. 4, Aug. 1987, pp. 323-344, USA.

Fig. 3

| $\vec{I_1}$ \ $\vec{I_2}$ | $\vec{a_1}$ | $\vec{b_1}$ | $\vec{c_1}$ | $\vec{d_1}$ |
|---|---|---|---|---|
| $\vec{a_2}$ | $\vec{r_{a1a2}}$ | $\vec{r_{b1a2}}$ | $\vec{r_{c1a2}}$ | $\vec{r_{d1a2}}$ |
| $\vec{b_2}$ | $\vec{r_{a1b2}}$ | $\vec{r_{b1b2}}$ | $\vec{r_{c1b2}}$ | $\vec{r_{d1b2}}$ |
| $\vec{c_2}$ | $\vec{r_{a1c2}}$ | $\vec{r_{b1c2}}$ | $\vec{r_{c1c2}}$ | $\vec{r_{d1c2}}$ |
| $\vec{d_2}$ | $\vec{r_{a1d2}}$ | $\vec{r_{b1d2}}$ | $\vec{r_{c1d2}}$ | $\vec{r_{d1d2}}$ |

USING DIFFERENT INDICATORS FOR DETERMINING POSITIONAL CHANGES OF A RADIOTHERAPY TARGET

RELATED APPLICATION DATA

This application is a national phase application of International Application No. PCT/EP2012/053718 filed Mar. 5, 2012 and published in the English language.

The present invention relates to the technical field of radiotherapy, in particular to the field of determining the position of a body part (referred to as target) which is to be treated (and therefore also referred to as "treatment body part"). Indicators are used as an indication for the changes in position of the target, in particular to determine the actual position of the target. The change of position of the indicator correlates with the change of position of the target. An indicator can be a detectable body part (referred to as "indicator body part") or a marker device (e.g. inside the body or attached to the outside of the body), in particular a single marker.

Reference is made to the patent applications EP 08 169 422.6 and EP 09 160 153.4 and the corresponding U.S. patent application Ser. No. 12/621,881 and U.S. Ser. No. 12/622,002 as well as WO 2011/107145. Disclosure of these applications is hereby incorporated by reference. Furthermore, it is referred to: Tong Lin et al.: "Tumor Targeting for Lung Cancer Radiotherapy Using Machine Learning Techniques" MACHINE LEARNING AND APPLICATIONS, 2008. ICMLA '08. Seventh International Conference on, IEEE, Piscataway, N.J., USA, 11 Dec. 2008, pages 533-538, XP31379459, ISBN: 978-0-7695-4395-4.

The present invention relates to the field of medicine and in particular to the use of radiation in order to treat parts of the body.

The present invention relates to the field of controlling a treatment beam. The treatment beam treats body parts which are to be treated, which are referred to in the following as "targets" or "treatment body parts". These body parts are in particular parts of a patient's body, i.e. anatomical body parts.

The present invention relates to the field of medicine and in particular to the use of beams, in particular radiation beams, to treat parts of a patient's body, which are also called treatment beams. Ionising radiation is in particular used for the purpose of treatment. In particular, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation are X-rays, high-energy particles (high-energy particle beams) and/or ionizing radiation emitted from a radioactive element. The treatment radiation, in particular the treatment beam, is in particular used in radiation therapy or radiotherapy, in particular in the field of oncology. For treating cancer in particular, parts of the body comprising a pathologic structure or tissue such as a tumour are treated using ionising radiation. The tumour is then an example of a treatment body part.

The treatment beam is preferably controlled such that it passes through the treatment body part.

The movements of the treatment body parts are in particular due to movements which are referred to in the following as "vital movements". Reference is also made in this respect to the above-mentioned applications EP 08 169 422.6 and EP 09 160 153.4, which discuss these vital movements in detail. In order to determine the position of the treatment body parts, analytical devices such as x-ray devices, CT devices or MRT devices are used to generate analytical images (such as x-ray images or MRT images) of the body. Analytical devices use in paricaular imaging methods and are in particular devices for analysing a patient's body, for instance by using waves and/or radiation and/or energy beams, in particular electromagnetic waves and/or radiation, ultrasound waves and/or particles beams. Analytical devices are in particular devices which generate images (for example, two-dimensional or three-dimensional images) of the patient's body (in particular, internal structures and/or anatomical parts of the patient's body) by analysing the body. Analytical devices are in particular used in medical diagnosis, in particular in radiology. However, it can be difficult to identify the treatment body part within the analytical image. It can in particular be easier to identify an indicator body part which correlates with changes in the position of the treatment body part and in particular the movement of the treatment body part. Thus, tracking an indicator body part allows a movement of the treatment body part to be tracked on the basis of a known correlation between the changes in the position (in particular the movements) of the indicator body part (also called "surrogate") and the treatment body part. Alternatively or additionally to the tracking of indicator body parts, marker devices (which can be used as an indicator and referred to as "marker indicators") can be tracked by using marker detection devices. The position of the marker indicators (e.g. fudiciary markers) have a known (predetermined) correlation with (in particular fixed relative position relative to) the position of indicator structures (like the thoraric wall (e.g. true ribs or false ribs) or diaphragm or bowel walls etc.) which in particular change their positions due to vital movements.

In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body. A tumour for example represents an example of a change in an anatomical structure. If the tumour grows, it may then be said to represent an expanded anatomical structure. Primary/high-grade brain tumours are for example usually visible on MRI scans when contrast agents are used to infiltrate the tumour. The MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernable in the image generated by the imaging method.

It is the function of a marker to be detected by a marker detection device (for example, a camera or an ultrasound receiver or analytical devices, like CT or MRI), such that its spatial position (i.e. its spatial location and/or alignment) can be ascertained. The detection device is in particular part known from a navigation system (IGS, image guided surgery). The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker device can for example be a reference star or a pointer or one marker or more than one (individual) markers which are preferably in a predetermined spatial relationship. A marker device comprises one, two, three or more markers which are in case of two or more markers in a predetermined spatial relationship. This predetermined spatial relationship is in particular acquired by the data processing method and for example stored in a computer of a treatment beam system.

It is an object of the present invention to determine the change of position of a target.

This object is solved by the subject-matter of the independent claims. The dependent claims are directed to advantageous embodiments. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

The inventor of the present invention has recognized that the vital movement of the target can be the result of more than one body structure (herein referred to as indicator structure) which performs a vital movement and that there can be a complex relationship between the movement of those indicator structures and the target. The inventor came to the conclusion that it is not appropriate to deal with indicators separately in order to establish separate correlations between the target and the respective indicator structures separately. For instance the position and the geometry (shape and/or size) of the lung is influenced not just by one indicator structure (e.g. diaphragm) but also by other indicator structures (for instance the true ribs and the false ribs). The diaphragm performs a cranial and caudal movement and the true ribs perform a anterior and posterior movement while the false ribs perform a lateral movement. However, the movement of the true ribs have for instance also a component in caudal and cranial direction so that the movement interferes with the cranial and caudal movement of the diaphragm. Furthermore, the deformation of the lung due to the different movements of the indicator structures couples the movements in the different directions. Thus, according to the invention, the change of position of several different indicator structures are preferably considered to determine the change of position (and/or geometry) of a target. The change of position (and/or geometry) of the target can in particular be determined based on a determination of the change of position and/or geometry of a structure (referred to as "target structure") in which the target is embedded. Examples for target structures and any kind of body structures in which a tumour can be embedded, for instance organs like lung, liver, breast, pancreas, bowel, uterus, ovary, and prostate. Movements of indicator structures can also be transferred via intermediate body structures (referred to as "coupling structures") to the target structure. For instance, the position of a target in a prostate (target structure) is influenced by the diaphragm (example for first indicator structure) and bowel walls (example for second indicator structure) although there are intermediate body structures. Also these coupling structures result in a complex relationship between positional changes of a set of different indicator structures and the positional changes of the target.

The indicator structures are in particular those structures the position of which is represented by muscles (like the diaphragm) which are in particular unconsciously controlled in particular by the brainstem. In the meaning of the present invention, indicator structures can also be body structures which are directly linked (in particular attached to) the muscles. In particular, the movement of indicator structures is directly linked to the movement of the (in particular unconsciously controlled) muscles. For instance the external intercostal muscles raise the top border of the thorax. For instance also the sternocleidomastoid muscle and the pectoralis minor muscles can influence the position of the ribcage and the sternum.

As far as in the following it is referred to the determination of change of a position of an object, this encompasses also the determination of the new position of the object after the change of position is performed. The determination of the new position can be performed based on the previous position (before the change of position) and the determined change of position. In particular, the inventive data processing method acquires start positions of the different objects (e.g. the target, the indicators, the indicator structures, etc) and the changes of the object are tracked starting from the known start positions using the method of the present invention. For determining a start position of the target for instance any of the methods described in the above-mentioned patent applications EP 08 169 422.6, EP 09 160 153.4 or WO 2011/107145 can be used. In particular 4D imaging methods (in particular a four-dimensional CBCT, 4D CBCT) can be used in order to determine the start position(s) of the target and/or indicator structures (in particular before the radiotherapy treatment). The method of the present invention acquires the start position(s) in order to track the target during radiotherapy. In particular, the indicators can be tracked and the claimed determination rule data can be acquired based on a measurement resulting from performing 4D imaging methods (e.g. a 4D CT or a 4D MR) of the patient's body to determine the position of the target and in particular to determine position of indicator body parts. Preferably for acquiring the determination rule data, alternatively or additionally to the determination of the position of the indicator body part, the position of marker indicators are acquired by means of marker detection devices in order to establish a known relative position between the indicators (indicator body parts and/or indicator markers) and the target. In this way a position set is preferably determined which describes relative positions between the indicators (marker indicator and/or indicator body parts) and the target and which can be used as starting point for tracking in accordance with the present invention.

In more detail, the present invention relates to a method (in particular tracking method) for determining the change of position of a target for performing radiotherapy treatment of a body of a patient. The method is in particular performed during treatment but can also be performed (in particular started) before treatment in particular for training purposes or for locking the inventive tracking method on the target (and to then continue the tracking during treatment). Locking on the target can in particular be assisted by a four-dimensional imaging method (like 4D CT or 4D MR).

The method preferably comprises a step of acquiring determination rule data. The determination rule data describe relationships between indicator position changes and target position changes and in particular relationship between indicator positions and the target position. The determination rule data describe in particular a correlation between the positional changes of a set of different indicators (more than one different indicator) and the positional change of the (single) target by mapping the (more than one) different positional changes to the (one) positional change of the target. Determination rule data can be determined based on measurement data generated by using analytical devices and/or marker detectors. In particular four-dimensional imaging methods are used in order to determine the position of the target in dependence on the time and to determine preferably simultaneously the corresponding positions of indicators by means of analytical devices and/or marker detectors. The analytical device and/or marker detectors are preferably used in order to correlate one of a plurality of possible positions of the target structure with a plurality of (more than one) different positions (a set of positions) of the indicators in particular for a plurality of different sets of positions of indicators. The determination rule data can be determined based on the measurement data generated from one patient or from a plurality of patients as will be described in more detail below. The determination rule data in particular describe a rule for deriving from positional changes of different indicators (linked to different indicator structures) the positional change of the target. The positional changes of the indicators represent an indicator change set and are described by data referred to as set data.

Preferably, the set data are acquired which describe a set referred to as "indicator change set". The indicator change set comprises more than one element and each of the elements represents information on changes of positions of indicators (for instance marker indicators or indicator body parts). That is, there is not just the positional change of one indicator which is used in accordance with the invention but a set of different information (physical information), in particular parameters describable by an n-tuple, which in particular represent values or vectors, in particular physical parameters which in particular describe the position of the indicators or the changes of position of the indicators. Preferably, the indicator change set includes elements which describe information on positions of different indicator structures. "Different" means herein in particular that the indicator structures are moved by different muscles or represent different muscles (which in particular move due to vital functions of the body). In particular, "different" means that the indicator structures move in different directions and in particular follow different trajectories in particular if subjected to vital movement.

The rule for mapping maps an indicator change set to one particular target change data describing one change of position of the (one) target and in particular the position of the target after the change. That is, elements of the change set which represent different indicator structure are mapped to the same target change data, in particular to the same change of the position of the target. The change of the position of an indicator structure is referred to herein also as "indicator structure change". The rules for mapping in particular depend on the positional changes described by the indicator change set. The rule for changes can also depend on the positions of the indicators before, during or after the change.

The aforementioned determination rule data are preferably established based on the aforementioned measurement of a patient and/or a pool of patients. The acquired determination rule data describe a rule for mapping an acquired indicator change set to the target change. That is, for instance that a set of positional changes of indicators can be used in order to determine the change of the target by applying the rule described by the determination rule data. The described rule is preferably a rule for mapping indicator change sets to target changes. In particular, the rule describes the rule for mapping respective ones of a plurality of indicator change sets to respective ones of a plurality of target changes. The rule for mapping results in that the application of the rule to an acquired indicator change set results in the determination of one target change. In other words, the elements of a indicator change set, to which the rule for mapping is applied, are all mapped to the same target change although two or more elements of the indicator change set represent changes of different indicator structures. In particular, the rule for mapping can be represented by a surjective, in particular injective function which turns one of the plurality of indicator change sets into one of a plurality of target changes. The plurality can be a plurality of distinct indicator change sets and/or target changes or can be a (continuous) multitude of indicator change sets and/or target changes. The rule is in particular constituted to be applicable for a range of acquired indicator change sets and/or for the corresponding range of target changes. The range is in particular limited, for instance to cover positional changes of the target less than 5 cm.

According to a further step of the method, the target change is determined based on the determination rule data and the set data by applying the rule described by the determination rule data to the acquired indicator change set.

Different indicator structures can cause different movements of the target. For instance in case the lung is the target structure, the vital movement of the true ribs can cause an anterior-posterior movement of the target, the vital movement of the false ribs can cause a lateral movement of the target and the diaphragm can cause a cranial and caudal movement of the target. Thus, a target can have movement in a particular direction which can be understood to be composed of different components of directions like a vector can be described by addition of several vectors pointing in different directions. According to the invention one of these added vectors can and in particular is correlated with more than one element of the change set representing different indicator structures. According to an aspect of the invention, the rule for mapping is constituted to correlate the direction of change of the target with more than one element of an indicator change set. That is two or more elements of the change set can influence the target change along the direction of the target change. Assuming that the elements of the change sets are represented by values and/or vectors which represent for instance a vector of positional change or a value of an amplitude of a cyclic movement along a trajectory, then, according to the rule for mapping, it is allowed and in particular described, at least for a subrange of target changes, that two or more values and/or vectors of two or more different elements representing information on positional changes (in particular representing positional changes) of two or more different indicator structures are used to determine the target change along that one direction of change of the target which is mainly caused by, in particular mainly linked with the movement of one of the different indicator structures.

In particular a mathematical relationship which links two or more of the elements (described by values and/or vectors) is used to describe the rule for mapping. For instance, a mathematical relationship between a component of movement of the true ribs along the cranial-caudal direction and the movement of the diaphragm along the cranial-caudal direction can be used in order to determine the target change. The mathematical relationship is in particular described by mathematical operators like addition, subtraction, multiplication, and division. The mathematical relationship may be described by a combination of the mathematical operators. For instance, an n-tuple $\vec{\Delta s}$ (in particular a vector) is described by the indicator change set and represents the positional change of different indicator structure and $\vec{\Delta r}$ is an n-tuple, in particular a vector which describes the positional change of the target, then the rule for mapping can be described for instance by:

$$\vec{\Delta r} = \underline{A} \cdot \vec{\Delta s},$$

where $\underline{A}$ is a matrix, the elements of which can be a function of the position $\vec{r}$ of the target before and/or after the change of position of the target and/or of the position $\vec{r}_i$ of indicators $I_i$ (before and/or after the change of positions of the indicators). In particular, the elements of the matrix can be a function of any of the parameters mentioned herein with respect to information on positions of the indicators, in particular frequency and/or amplitude of cyclic movements of one or more of the indicators and the parameters mentioned below with respect to supplemental information. The n-tuple $\vec{\Delta r}$ describes the information on change of position of the target and can include elements which describe just the change of position of the target or includes for instance elements which describe both the change of position of the target and the position of the target. The n-tuble $\vec{\Delta s}$ can include elements which describe just the changes of positions of the indicators or both the changes of positions of the indicators and the positions of the indicators. The n-tuble $\vec{\Delta s}$ describes the information on changes of positions of the indicators. Preferably, as mentioned above, the rule for mapping considers complex influences, in particular complex interfering influences of the movement of indicator structures on the movement of the target. Therefore the matrix $\underline{A}$ is preferably constituted so that there is no reference system in which the matrix $\underline{A}$ becomes a diagonal matrix. As a further example for a mathematical relationship, the amount of positional change for the target $|\vec{\Delta r}|$ or one or more components of $\vec{\Delta r} = (\Delta x, \Delta y, \Delta z)$ as for instance $\Delta x$ can be a function of one or more elements $\Delta s$ of the indicator change set $\vec{\Delta s}$, for instance $$|\vec{\Delta r}| = f\frac{\Delta s_i}{\Delta s_j}, \text{ or } |\vec{\Delta x}| = f\frac{\Delta s_i}{\Delta s_j},$$

in particular $$|\vec{\Delta r}| = k\frac{\Delta s_i}{\Delta s_j},$$

where k is a constant and $\Delta s_i$ and $\Delta s_j$ are elements of the indicator change set describing an amount of change of a position of an indicator $I_i$ and another different indicator $I_j$ (following a different trajectory and representing the movement of a different indicator structure).

The information on the change of positions of the indicators (describable by the n-tuple $\vec{\Delta s}$) includes in particular at least one of the following information: the change of position of the indicator, a change of position within a trajectory followed by the indicator, a change of direction of movement of the indicator, and a change of amplitude of a cyclic movement of the indicator. The aforementioned information is also referred to as positional information. Additionally, the information on the change of position of the indicators (describable by the n-tuple $\vec{\Delta s}$) can also include time related information like the time which passed during the change of position of the indicator indicated by the indicator change set.

In particular, the information on the changes of the positions of the indicator (describable by the n-tuple $\vec{\Delta s}$) can include information on the position $\vec{r}_i$ of the indicators before and/or after the change of position, in particular on the amplitude of a cyclic movement of the indicator which was given before and/or after the change. In particular information on the changes can comprise the current frequency of a cyclic movement, in particular the current maximum amplitude of a cyclic movement at the time of the change. In particular, the target change can differ in dependence on the given positions $\vec{r}_i$ of the indicators in particular within respective trajectories or in dependence on the given position $\vec{r}$ of the target when the change of position of the indicators occurs. In particular, a change of position of the same amount of elements of an indicator change set can have a different effect on the target change in dependence on the different position $\vec{r}_i$. In particular, it can be dependent on whether indicators represented by the elements are close to a maximum amplitude or in the middle between the two maxima of a cyclic movement. It can also depend on the maximum amplitudes of the indicators. For instance, the same change of amplitude of one indicator which represents breast breathing can result in a different target change in dependence on whether the breast breathing is supplemented by abdominal breathing or not.

Additional information (referred to as "supplemental information") which also can be described by the information on the change of positions of the indicators and which can be considered by the determination rule data according to a further embodiment of the invention are maximum amplitude of a cyclic movement of an indicator along a trajectory, frequency of the cyclic movement, a medical information on the target and the indicators like type of the target (for instance type of tumor), position of the target within the target structure, type of indicator structures represented by the indicators in particular principle directions of movements of the indicator structures and medical categorization of the indicators like the medical name of the indicator structures like false ribs or diaphragm or name of the muscle structure, false ribs, true ribs or organ involved in the vital movement like heart or bowel.

According to an embodiment of the invention, the rule for mapping is based on correspondence data which describe a correspondence between indicator change sets and corresponding target changes. The correspondence data can be implemented as one or more lookup tables. In particular, an interpolation is performed between entries in the lookup table if the acquired indicator change set is not identical with one of the entries in the lookup table. The correspondence data can be in particular generated by measuring the positional changes of the indicator (referred to as "indicator changes") for different maximum amplitudes and/or frequencies of cyclic movements of the indicators and by measuring the positions of the indicators for a plurality of positions within a movement along a cyclic trajectory. In particular, the rule for mapping can comprise different lookup tables for different sets of maximum amplitudes and/or for different frequencies of the cyclic movements of the indicators. That one of the lookup table is selected which corresponds to the set of maximum amplitudes or the frequency as described by the indicator change sets. In case of no exact correspondence, an interpolation between the lookup tables is performed.

The measurement of indicator change sets is preferably performed in combination with a measurement of the position of the target so that each target position is assigned to a set of positions of the indicators and thus each change of position of the target (and preferably the position of the target before the change) can be assigned to an indicator change set (which includes in particular in addition to information on the positional change of the indicator also information on the position of the indicator before the change). The correspondence data can be generated from an individual patient in particular by using the aforementioned four-dimensional imaging methods and using the aforementioned analytical devices for detecting the position of the target and optionally also for detecting the position of the indicators. For detecting the position and the positional changes of the marker indicators also marker detection devices can be used. The aforementioned correspondence data which describes the correspondence between the indicator change sets and the target changes are referred to as "indicator target correspondence data". Depending on whether they are based on measurement performed on an individual patient which comprises a target to be treated they are referred to as "individual indicator target correspondence data" and if they are based on the plurality of different patients (pool of patients) having a similar target they are referred to as "generic target correspondence data". "Similar target" means in particular, that the target is of the same medical type (for instance the same type of tumor), in particular that the target has the same relative position within the same target structure (for instance the same position within the lung, if the lung is the target structure), and in particular that the patient has about the same medical condition (e.g. same age, same breathing pattern, etc.) and in particular if the target extends from one (first) body structure to a next (second) body structure or not. In the first case, the target structure consists of the first body structure. In the latter case, the target structure consists of the first and second body structure and the extension can have an influence on the positional changes of the target if the first and second body structure move differently due to vital movements. For instance a lung cancer can have grown from the lung (first body structure) to the chest wall (second body structure).

Similarity measures and/or similarity thresholds can be applied to determine whether the target is similar or not.

According to a further embodiment, the change of position and/or of the geometry of the target structure is determined in an intermediate step in dependence on the indicator change set and then, in a next step, the change of position of the target (target change) is determined based on the change of position and/or geometry of the target structure. The change of geometry of a target structure can have an influence on the position of a target since the change of geometry can result in compression of parts of the target structure and expansion of other parts of the target structure which result in a movement of the target. This influence of the geometry on the position can for instance be determined by using a model of the target structure (for instance a visco-elastic model of the target structure or an elastic model of the target structure). The model models in particular the mechanical response of the inner structure of the target structure to a deformation and/or displacement of the boundary of the target structure. The model describes in particular a mechanical response of the target structure (the inner structure of which can be of for instance visco-elastic nature) to changes in the boundary of the target structure which changes are linked with the indicator change sets. The model describes in particular the inner structure of the target structure and can in particular be described by a stress-strain curve of the target structure, stress relaxation behavior and creep behavior of the target structure. The data on the geometry (in particular the boundary) of the target structure can be acquired by imaging methods performed by analytical devices as mentioned above. How to model an organ is for instance described in James C Ross et al: "Real-Time Liver Motion Compensation for MrgFUS" Medical Image Computing and Computer-Assisted Intervention MICCAI 2008; Lecture Notes in Computer Science, Springer Berlin, Heidelberg, Bd. 5242, 6. September 2008, Seiten 806-813, XP19105238, ISBN: 978-3-540-85989-5; and "Modelling Organ Deformation using Mass-springs and Tensional Integrity" by Pierre-Frédérik Villard, Wesley Bourne, and Fernando Bello. The disclosure of the papers is incorporated herein by reference.

The aforementioned model can in particular include assumptions on an elasticity module. The model can in particular be generated based on a plurality of measurements of positional changes and changes of geometry of the target structure of the individual patient or of a plurality of patients having a similar target.

The model in particular depends on the type of the target structure. The type of the target structure in particular also depends on the functional type of the body structure, the type of the organ, the density of the body structure, the position of the body structure within the body, deformability of the body structure, elasticity of the body structure (rigid or not rigid) etc.

According to the aforementioned embodiments, preferably the position of the target within the target structure is acquired by acquiring data referred to as "target position data" which describes this position. The target position data are preferably based on the aforementioned starting position when the inventive tracking method starts and can be acquired so that it corresponds to the position of the target determined by the method before considering the current changes of positions of the indicators. Furthermore, preferably the geometry and/or the position of the target structure within the body is described by target geometry data. Preferably, the rule for mapping considers the target position data and/or the target geometry data.

According to the embodiment, the rule for mapping is further based on correspondence data which describe the correspondence between indicator change sets and the corresponding changes (changes of position and/or geometry) of the target structure. The change of target structure can for instance be described by a change of the position and/or geometry (shape and/or size) of the boundary of the target structure. The correspondence data are referred to as target structure correspondence data. If the target structure correspondence data are based on measurement of the individual patient which includes the target to be treated, the correspondence data are referred to as "individual target structure correspondence data". The individual target structure correspondence data can in particular be generated by measuring the positions and/or the geometries of the target structure for different indicator change sets which can be provoked for instance by provoking a different amplitude and/or frequency of breathing and/or heartbeat and by provoking different types of breathing like abdominal respiration or breast breathing.

Alternatively to or in addition to the individual target structure correspondence data, the rule for mapping can also be based on generic target structure correspondence data which describe a correspondence between indicator change sets and corresponding target structure changes generated by measuring the correspondence for a plurality of different patients. The patients have preferably a target of the same type as mentioned above (in particular the same position within the target structure, the same target structure, and the same target type (for instance type of tumor, in particular the same tumor classification)).

By using the target structure model, the target change can be determined based on the acquired indicator change set and the (individual and/or generic) target structure correspondence data. In particular, the target structure change is determined based on the target structure correspondence data and the indicator change set. Then, the target change is determined based on the determined target structure change, the target structure model and optionally the target position data.

Generally, the determination of the target change from the change of the position and/or geometry of the target structure (referred to as "target structure change") can be prescribed by a rule referred to as "sub-rule" which maps the target structure change to the target change. The target structure change can describe not just the change of the position and/or change of geometry of the target structure but also the position and/or geometry of the target structure.

The sub-rule can be based on the above-mentioned model referred to as target structure model. The target structure model describes preferably physical parameters of the target structure which rule a change of the inner structure of the target structure due to the target structure change. For instance, the target structure can be modeled by a grid comprising nods which are linked. The links can for instance behave in an elastic or viscoelastic manner. The target structure model models in particular the change of the position (and in particular of the geometry) of the target within the target structure due to the change of the inner structure. The modeling of the target change is preferably performed in dependence on the target position data, for instance in dependence on the position of the target within the aforementioned grid and optionally also in dependence on target geometry data.

According to another embodiment, the sub-rule is based on an elastic fusion. In particular a model of the target structure which represents the target structure before the target structure change can be used as a starting point. The model can be for instance a two-dimensional or three-dimensional image of the target structure which results from one of the aforementioned imaging methods. Thus, the elastic fusion is in particular an image fusion. The change of the position and/or geometry of the boundary of the target structure can be determined based on the target structure correspondence data and the indicator change set. After determining the changed boundary, the target structure model can be subjected to elastic fusion to fit into the changed boundary. Thus, the model of the target structure before the target structure change can be fused to a target structure after the target structure change. The model of the target structure preferably includes the target. Thus, by fusing the model of the target structure to fit into the changed boundary, the position of the target within the target structure is also changed. Thus, the target change can be determined by performing the elastic fusion. To this end, preferably the target position data are used which preferably describe the position of the target within the target structure model before the target structure change.

According to another embodiment, the sub-rule is based on correspondence data which describe a correspondence between a plurality of different target structure changes and the corresponding target changes. As described previously, such data can be generated by performing measurements on an individual patient for a plurality of different positions and/or geometries of the target structure, in particular by using imaging methods performed by the analytical device. The measurements can be performed on the individual patient which includes the target to be treated and/or on a plurality of patients of a patient pool which fulfils conditions for similarity of the target type as described above.

Of course, the aforementioned sub-rules can be combined to determine the target change. The above-mentioned target change represents data which describe information on the change of position of the target. This information describes in particular the change of position of the target from a previous position which adopts the target before the change to a subsequent position which adopts the target after the change. The data referred to as target change data can also describe the previous and/or the subsequent position. In particular, according to an embodiment, the target change data describes the position of the target which is adopted after changes of positions of indicators. That is, the change of position is described by describing the previous position and the subsequent position. Furthermore, the target change data can be used as target position data in a next step of the inventive tracking method. Correspondingly, the indicator change set can describe the previous positions and the subsequent positions of indicators which the indicators adopt previous to the change and subsequent to the change, respectively. The rule for mapping can in particular map previous positions of indicators to previous positions of the target and can map subsequent positions of the indicators to a subsequent position of the target. In other words, the present invention does not just cover relative changes of positions but is also constituted to determine an absolute position of the target based on the indicator change set, the rule for mapping and the target change data determined in a previous step (before the current change is considered).

The positions of the indicators and/or of the target can be described in a reference system. The reference system is for instance a reference system in which the treatment device which is used for radiotherapy treatment is at rest or in which parts of the body of the patient (for instance the target, the target structure, an indicator structure or other parts of the body like the spine) are at rest or for instance in which the room in which the radiotherapy is performed is at rest. In this respect it is also referred to the already mentioned applications EP 2 189 940, EP 2 189 943 and WO 2011/107145.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit—CPU) which executes the computer program elements and optionally a volatile memory (in particular, a random access memory—RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term of computer encompasses a cloud computer, in particular a cloud server. The term of cloud computer encompasses cloud computer system in particular comprises a system of at least one cloud computer, in particular plural operatively interconnected cloud computers such as a server farm. Preferably, the cloud computer is connected to a wide area network such as the world wide web (WWW). Such a cloud computer is located in a so-called cloud of computers which are all connected to the world wide web. Such an infrastructure is used for cloud computing which describes computation, software, data access and storage services that do not require end-user knowledge of physical location and configuration of the computer that delivers a specific service. In particular, the term "cloud" is used as a metaphor for the internet (world wide web). In particular, the cloud provides computing infrastructure as a service (IaaS). The cloud computer may function as a virtual host for an operating system and/or data processing application which is used for executing the inventive method. Preferably, the cloud computer is an elastic compute cloud (EC2) provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

Preferably, the inventive method is at least partly executed by a computer. That is, all steps or just some of the steps (i.e. less than a total number of steps) of the inventive method may be executed by a computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information".

The present invention is also directed to a method for controlling a treatment beam based on the determined target change data.

The present invention is also directed to a treatment beam system. The treatment beam system comprises a treatment device. The treatment device is constituted to emit the treatment beam. Furthermore, the treatment beam system comprises the computer on which the aforementioned program is running or into which the aforementioned program is loaded. Thus, the computer performs the method of the present invention. In particular, the computer determines the target change data based on the acquired indicator set data. Furthermore, the treatment beam system comprises the treatment device which is constituted to emit a treatment beam and is further constituted to control the position of the treatment beam in accordance with the target change data determined by the computer. For instance, the computer transmits the target change data to the treatment device.

Additional features and advantages of the present invention are disclosed in the following detailed description of embodiments of the invention.

FIG. 3 shows a lookup table for determination of the position of the target in dependence on indicator positions.

Figure 1:
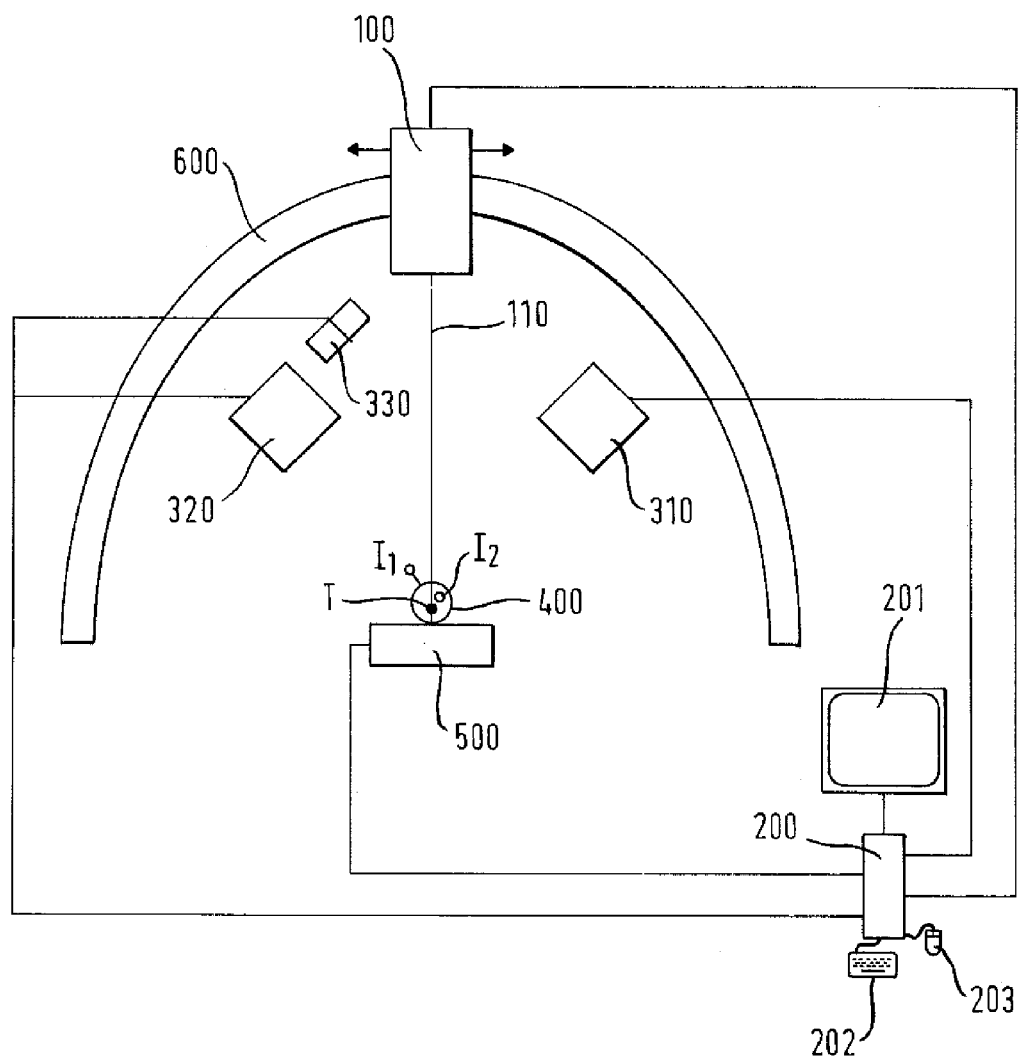
FIG. 1 shows a treatment beam system.

FIG. 1 shows a treatment beam system in accordance with the invention. A treatment device 100 emits a treatment beam 110. The treatment device 100 can be moved as indicated by the arrows, thus guiding the treatment beam 110. A computer 200 is electrically connected to the treatment device 100 in order to control the guidance of the treatment beam 110 by means of control signals. A screen 201, a keyboard 202 and a mouse 203 are connected to the computer 200. The computer 200 also controls analytical devices 310 and 320. The analytical devices 310 and 320 are in particular x-ray devices which take x-ray images of a patient 400. The computer 200 is connected to the analytical devices 310 and 320 in order to receive advance image data (before the treatment) and process image data (during the treatment) from the analytical devices 310 and 320. In particular, the computer 200 is also configured to control the image acquisition performed by the analytical devices 310 and 320. There is preferably an electrical connection between the analytical devices 310 and 320 and the computer 200 in order for the computer 200 to send control signals to the analytical devices 310 and 320 and/or receive the aforementioned data from the analytical devices 310 and 320. The patient 400 is lying on a table 500. The analytical devices 310 and 320 and the treatment device 100 are supported by a support structure 600. According to a further embodiment, the analytical devices 310 and 320 are separate from the treatment device, in particular mounted separately. In order to control the relative position between the treatment beam 110 and the patient 400, it is also possible to move the table 500 so as to reposition the patient 400 relative to the treatment beam 110. In short, the treatment beam system is preferably configured to control the position of the treatment beam 110, in particular relative to the patient 400. This is in particular performed by the computer 200. Additional, assisting control devices can for instance be integrated into the treatment device 100 and/or the table 500 and preferably cooperate with the computer 200.

The computer 200 preferably has also information on the imaging geometry of the analytical devices 310 and 320 relative to the location of the treatment beam 110.

The information on the imaging geometry preferably comprises information which allows the analysis image (x-ray image) to be calculated, given a known relative position between the imaging geometry analysis apparatus and the analysis object (anatomical body part) to be analysed by the x-ray radiation, if the object (anatomical body part) to be analysed is known, wherein "known" means that the spatial geometry (size and shape) of the analysis object is known. This means in particular that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The position and in particular orientation of the imaging geometry is in particular defined by the position of the x-ray device, in particular by the position of the x-ray source and the x-ray detector and/or in particular by the position of the multiplicity (manifold) of x-ray beams which pass through the analysis object and are detected by the x-ray detector. The imaging geometry in particular describes the position (in particular, the orientation) and the shape (for example, a conical shape exhibiting a specific angle of inclination) of said multiplicity (manifold). The position can in particular be represented by the position of an x-ray beam which passes through the centre of said multiplicity or by a position of a geometric object (such as a truncated cone) which represents the multiplicity (manifold) of x-ray beams. Information concerning the above-mentioned interaction is preferably three-dimensionally known, for example from a three-dimensional CT, and describes the interaction in a spatially resolved way for points and/or regions of the analysis object, in particular force all of the points and/or regions of the analysis object. Knowledge of the imaging geometry in particular allows a location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made in particular to the following publications:

1. "An Efficient and Accurate Camera Calibration Technique for 3D Machine Vision", Roger Y. Tsai, Proceedings of the IEEE Conference on Computer Vision and Pattern Recognition. Miami Beach, Fla., 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344. See also http://www.cs.cmu.edu/~rgw/TsaiDesc.html
3. Publication by Ziv Yaniv, "Fluoroscopic X-ray Image Processing and Registration for Computer-Aided Orthopedic Surgery"
4. EP 08 156 293.6
5. U.S. 61/054,187

Preferably based on the imaging geometry information, the computer calculates the location of the treatment beam 110 relative to the target (treatment body part). By comparing the position determined for the treatment beam and the position determined for the target, the position of the treatment beam can be controlled so as to hit the target.

The target change data determined in accordance with the method described herein, are preferably used to correctly control the position of the treatment beam 110 relative to the patient 400. A program which represents an implementation of said method is preferably stored and/or running on the computer 200. An indicator $I_1$ can be a marker which is attached to a part of the body (for instance to the breast in order to track movements of the true ribs). Another indicator $I_2$ is for instance the diaphragm, the position of the which is tracked by means of the analytical devices 310 and 320. The target T is hit by the treatment beam 110. The position of the marker $I_1$ can be for instance detected by a (stereotactic) camera as known from navigation systems. Preferably at least two indicators are used which respectively represent different vital movements of indicator structures. In order to determine a start position of the tumor movement and in order to correlate the start position of the tumor movement with the positions of the indicators ($I_1$, $I_2$), for instance a CBCT image can be generated in order to determine the position of the tumor in a reference system in which in particular trajectories of the indicators and/or the target is at rest. Preferably, simultaneously to the determination of the position of the tumor by an analytical device (for instance CBCT) the positions of the indicators (for instance $I_1$ and $I_2$) is determined. The changes of the position of the tumor can then be determined by determining the target change data in accordance with the present invention and the position of the target can be determined based on the start position of the target and the determined change of the position of the target (target change data).

Figure 2:
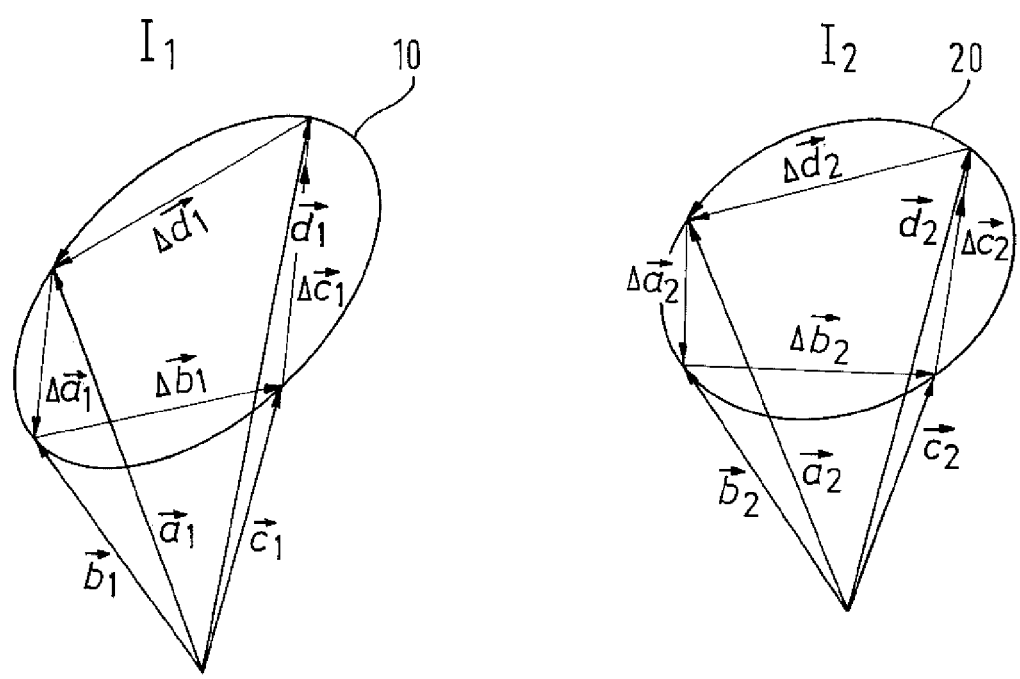
FIG. 2 shows trajectories, positions, and positional changes of indicators I1 and I2.

FIG. 2 shows a cyclic trajectory 10 of a first indicator $I_1$ on the left side and a cyclic trajectory 20 of a second indicator $I_2$ on the right side. Positions on the trajectory path of the first indicator $I_1$ are described by vectors $\vec{a}_1$, $\vec{b}_1$, $\vec{c}_1$ and $\vec{d}_1$. The n-tuple ($\vec{a}_1$, $\vec{b}_1$, $\vec{a}_2$, $\vec{b}_2$) is an example for $\overrightarrow{\Delta s}$ and describes the information on changes of positions of the indicators $I_1$ and $I_2$. The changes of positions of the indicator $I_1$ between the different aforementioned positions are indicated by $\overrightarrow{\Delta a}_1$, $\overrightarrow{\Delta b}_1$, $\overrightarrow{\Delta c}_1$ and $\overrightarrow{\Delta d}_1$. The different positions of the indicator along the cyclic trajectory can be described in a reference system in which the trajectory is at rest. In the same manner, the right side of FIG. 2 shows a cyclic trajectory of the second indicator $I_2$. Distinct positions along the trajectory 20 are indicated by vectors $\vec{a}_2$, $\vec{b}_2$, $\vec{c}_2$ and $\vec{d}_2$. The positional changes between these positions are indicated by the following vectors: $\overrightarrow{\Delta b}_2$, $\overrightarrow{\Delta b}_2$, $\overrightarrow{\Delta c}_2$ and $\overrightarrow{\Delta d}_2$. Again, the vectors describing the positions can be described in a reference system in which the trajectory 20 is at rest. Preferably, the trajectories of indicators (for instance $I_1$ and $I_2$) are described in a reference system in which the trajectories are at rest.

According to an embodiment, correspondence data which describe a correspondence between the positions of the indicators $I_1$ and $I_2$ and optionally further indicators and the positions of the targets $\vec{r}$ are generated based on a measurement of positions of the indicators along the trajectories and a corresponding (in particular simultaneous) measurement of the position of the target. The measurements are in particular performed before the treatment for instance by using four-dimensional imaging methods. A simplified example of indicator target correspondence data is shown in a simplified lookup table in FIG. 3. In the upper line, the vector $\vec{I}_1$ represents the position of the indicator $I_1$. In the table, four positions of the target $I_1$ are: $\vec{a}_1$, $\vec{b}_1$, $\vec{c}_1$ and $\vec{d}_1$. Those positions are written in the upper line of the lookup table. The left column of the lookup table of FIG. 3 shows positions $\vec{I}_2$ of the indicator $I_2$: $\vec{a}_2$, $\vec{b}_2$, $\vec{c}_2$ and $\vec{d}_2$. The lookup table in FIG. 3 shows which position $\vec{r}$ of the target corresponds to which positions of the two indicators $I_1$ and $I_2$. For instance, the position $\vec{r}_{b1c2}$ corresponds to the indicator positions $\vec{b}_1$ and $\vec{c}_2$. If for instance the previous position of the target is $\vec{r}_{a1a2}$ and the current position is $\vec{r}_{b1b2}$, then the n-tupe $\overrightarrow{\Delta r}$ which describes information on change of the is target is for instance ($\vec{r}_{a1a2}$, $\vec{r}_{b1b2}$).

The change of the position of the indicator $I_1$ is denoted as $\overrightarrow{\Delta I}$. The change of the position of the indicator $I_1$ is denoted for instance as $\overrightarrow{\Delta I}_1$ and the change of position of the indicator $I_2$ is denoted as $\overrightarrow{\Delta I}_2$. That is, an indicator change set $\overrightarrow{\Delta s}$ can for instance also be described as ($\overrightarrow{\Delta I}_1$, $\overrightarrow{\Delta I}_2$). A change set can also include information on the positions of the indicators, that is an example for an indicator change set $\overrightarrow{\Delta s}$ is also: ($\vec{I}_1$, $\overrightarrow{\Delta I}_1$, $\vec{I}_2$, $\overrightarrow{\Delta I}_2$). Specific examples for a change set are for instance ($\vec{a}_1, \vec{\Delta a}_1, \vec{a}_2, \vec{\Delta a}_1$) or ($\vec{a}_1, \vec{b}_1, \vec{a}_2, \vec{b}_2$). The changes of positions can also be derived from the latter example since for instance $\vec{\Delta a}_1 = \vec{b}_1 - \vec{a}_1$.

In order to generate the lookup tables for instance also a plurality of patients (patient pool) can be used which have the same type of target to be treated, in particular at the same position within the same target structure. Preferably the same indicators (in particular indicators positioned at the same positions with respect to the body) are used to determine trajectories of indicators. Such trajectories of indicators are preferably averaged in order to generate a generic trajectory for each of the different type of indicators. On the basis of the generated generic trajectories, the generic correspondence data can be generated. The examples shown in FIG. 3 represents an example for indicator target correspondence data. In case those indicator target correspondence data are generated based on measurements performed on the patient to be treated, those are referred to as individual indicator target correspondence data. If they are generated by using a patient pool, they are referred to as generic indicator target correspondence data.

Figure 4:
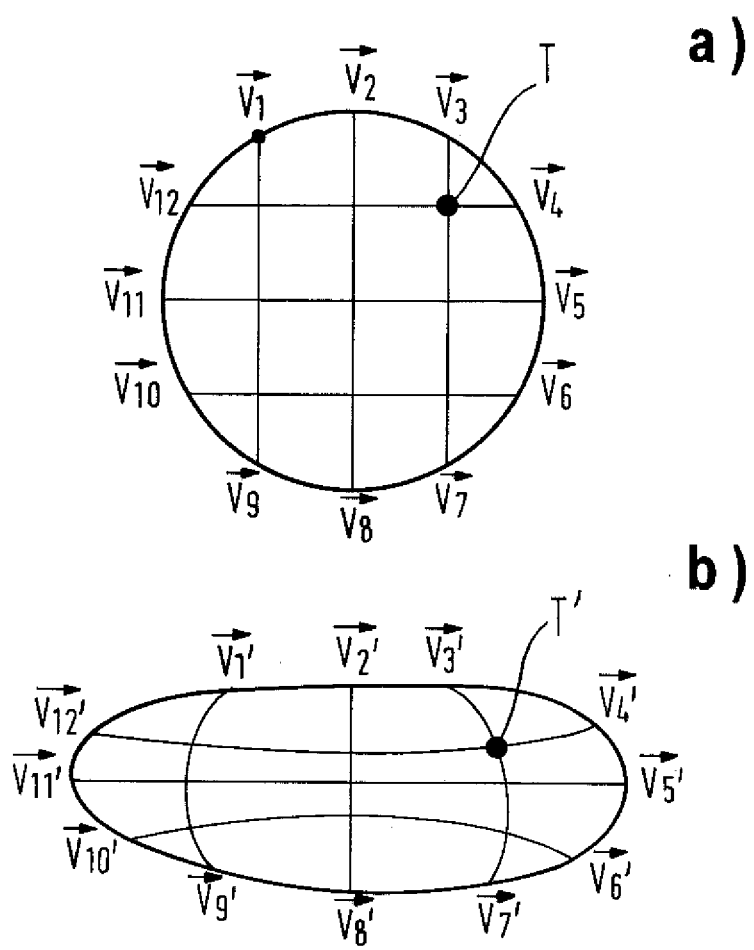
FIG. 4 shows a modeled movement of the target due to deformation of a target structure.

FIG. 4a) shows a model of a target structure. The model includes a grid which represents the inner structure of the target structure. The gridlines are assumed to have an elastic behavior (e.g. like a spring) if the boundary is compressed or expanded. The target T is placed within the model. Preferably, the gridlines are selected so that the target is placed at a node established by the gridlines. The model is preferably three-dimensional. For simplicity, just a two-dimensional simplified model is shown in FIG. 4. The gridlines touch the boundary of the model at positions $\vec{v}_1$ to $\vec{v}_{12}$ referred to as positions of boundary points or just boundary positions. According to an embodiment, target structure correspondence data are provided for instance by using a lookup table. The lookup table describes the relationship between the positions of the indicators and the boundary positions $\vec{v}_1$ to $\vec{v}_{12}$. In the example give, FIG. 4a) shows the boundary of the model of the target structure before the change and FIG. 4b) shows the boundary of the target structure of the model after the change. In the example given in FIG. 4, the model is compressed in the vertical direction and expanded in the horizontal direction. This results in a change of position of the target T downward and to the right. The deformation of the target structure can be for instance caused by a neighboring body structure which is above the target structure and moves downwards. As can be seen, such a downward movement can not just result in a downward movement by the target but also in a movement of the target to the right. This is due to the mechanical response of the target structure and explains the complex relationship between such a movement of the target structure and the movement of indicator structures and the indicators.

The boundary positions $\vec{v}_1$ to $\vec{v}_{12}$ are denoted as $\vec{v}_1'$ to $\vec{v}_{12}'$ in FIG. 4b). The boundary positions $\vec{v}_1'$ to $\vec{v}_{12}'$ represent the positions of the boundary points after the change. The reference sign T' represents the position of the target after the change.

Assuming that the grid shown in FIG. 4a) represents an image of the target structure, then the grid shown in FIG. 4b) is an example for fusing the image of FIG. 4a) within the boundary of the target structure shown in FIG. 4b). Due to this elastic fusion also the position of the target changes from T to T'.

The invention claimed is:

1. Method for tracking a target during radiotherapy treatment, the tracking being performed based on data referred to as target change data, the target change data describing information on the change of position of a target included in a body of a patient, a body structure in which the target is embedded being referred to as target structure, the method being performed by a computer and comprising:
   acquiring determination rule data describing a rule for mapping an indicator change set to the target change data, the indicator change set comprising more than one element, the elements of the indicator change set respectively representing information on respective changes of positions of indicators, at least two of the indicators respectively indicating a change of position of different body structures referred to as indicator structures;
   acquiring set data describing an acquired indicator change set;
   modelling, via a model of the target structure, a mechanical response of the target structure to changes in a boundary of the target structure, the changes being linked with the indicator change set;
   determining a change of geometry and/or position of the target structure based on the indicator change set;
   determining the target change data based on the determination rule data and the set data by applying the rule for mapping to the acquired indicator change set; and
   tracking the target based on the determined target change data.

2. The method of claim 1, wherein the determined target change data describes at least one of the following:
   the change of position of the target;
   the change of position of the target and the position of the target before the change; and
   the position of the target after the change.

3. The method of claim 1, wherein the information on respective changes of positions of the indicators describe positional changes of the indicators and the positions of the indicator when the change occurs and wherein the rule for mapping depends on the positions of the indicators.

4. The method of claim 1, wherein the rule for mapping comprises a mathematical relationship between elements of the acquired indicator change set to be mapped.

5. The method of claim 1, wherein a change of position and/or geometry of the target structure is referred to as target structure change;
   wherein the rule for mapping is further based on individual target structure correspondence data which describe a correspondence between a plurality of different indicator change sets and the corresponding target structure changes, the individual target structure correspondence data have been generated by analyzing the body of the patient to be treated;
   wherein the target structure change is determined based on the acquired indicator change set and the individual target structure correspondence data;
   wherein the rule for mapping is further based on a sub-rule which is based on the model and describes a rule for mapping the determined target structure change to the target change data; and
   wherein the target change data is determined based on the determined target structure change and the sub-rule.

6. The method of claim 1, wherein a change of position and/or geometry of the target structure is referred to as target structure change;

wherein the rule for mapping is further based on generic target structure correspondence data which describe a correspondence between a plurality of different indicator change sets and the corresponding target structure changes, the generic target structure correspondence data have been generated by analyzing the body of a plurality of different patients;

wherein, the target structure change is determined based on the acquired indicator change set and the generic target structure correspondence data;

wherein the rule for mapping is further based on a sub-rule which is based on the model and describes a rule for mapping the determined target structure change to the target change data; and wherein the target change data is determined based on the determined target structure change and the sub-rule.

7. The method of claim 5, comprising:

acquiring target position data describing the position of the target within the target structure before the change;

wherein the sub-rule comprises the target structure model which describes physical parameters of the target structure which rule a change of an inner structure of the target structure due to a change of a boundary of the target structure and which models a change of position of the target within the target structure due to the change of the inner structure based on the target data; and wherein the determination of the target change data is further based on the target data.

8. The method according to claim 1, wherein a change of position and/or geometry of the target structure is referred to as target structure change, wherein the model is an image of the target structure and the rule for mapping comprises a sub-rule which is based on elastically fusing the model image of the target structure, which represents the target structure including the target before the change of the target structure, to an image of the target structure which results from the determined change of the target structure.

9. The method of claim 1, wherein the indicators, the movements of which are represented by the elements of the acquired change set, include at least two of the following indicators: a first indicator which moves in accordance with diaphragm movement, a second indicator which moves in accordance with false ribs, and a third indicator which moves in accordance with true ribs, a fourth indicator which moves in accordance with heart beat, and a fifth indicator which moves in accordance with bowel movements.

10. A system for administering radiotherapy treatment to a tracked target, the target tracked based on data referred to as target change data, and the system comprising:

a processor and a memory; and a treatment device configured to emit a treatment beam;

wherein a body structure in which the target is embedded being referred to as target structure, and wherein the processor is configured to:

acquire, from the memory, determination rule data describing a rule for mapping an indicator change set to the target change data, the indicator change set being a set which comprises more than one element, the elements of the indicator change set respectively representing information on respective changes of positions of indicators, at least two of the indicators respectively indicating a change of position of different body structures referred to as indicator structures;

acquire set data describing an acquired indicator change set;

model, via a model of the target structure, a mechanical response of the target structure to changes in a boundary of the target structure, the changes being linked with the indicator change set;

determine a change of geometry and/or position of the target structure based on the indicator change set;

determine the target change data based on the determination rule data and the set data by applying the rule for mapping to the acquired indicator change set;

track the target based on the determined target change data; and control the position of the treatment beam in accordance with the determined target change data.

11. A method for controlling a position of a treatment beam by determining data referred to as target change data which can be used for performing radiotherapy treatment, the target change data describing information on the change of position of a target included in a body of a patient, a body structure in which the target is embedded being referred to as target structure, the method comprising:

acquiring determination rule data describing a rule for mapping an indicator change set to the target change data, the indicator change set being a set which comprises more that one element, the elements of the indicator change set respectively representing information on respective changes of positions of indicators, at least two of the indicators respectively indicating a change of position of different body structures referred to as indicator structures, acquiring set data describing an acquired indicator change set;

modelling, via a model of the target structure, a mechanical response of the target structure to changes in a boundary of the target structure the, changes being linked with the indicator change set;

determining a change of geometry and/or position of the target structure based on the indicator change set;

determining the target change data based on the determination rule data and the set data by applying the rule for mapping to the acquired indicator change set;

tracking the target based on the determined target change data; and controlling the position of the treatment beam on the basis of the determined target change data.

12. The method of claim 6, comprising the step of:

acquiring target position data describing the position of the target within the target structure before the change;

wherein the sub-rule comprises the target structure model which describes physical parameters of the target structure which rule a change of an inner structure of the target structure due to a change of a boundary of the target structure and which models a change of position of the target within the target structure due to the change of the inner structure based on the target data; and wherein the determination of the target change data is further based on the target data.

13. The method of claim 3, further comprising:

acquiring target position data which describe the position of the target before the change of position of the target and wherein the rule for mapping depends on the target position data.

14. The method of claim 3, wherein the information on respective changes of positions of the indicators describe positional changes of the indicators and the maximum amplitude of the positional changes, and/or the frequency of the positional changes if the indicators are subjected to cyclic movements; and
  wherein the rule for mapping depends on the positional changes of the indicators and the maximum amplitude of the positional changes and/or the frequency of the positional changes.

15. The method of claim 13, wherein the information on respective changes of positions of the indicators describe positional changes of the indicators and the maximum amplitude of the positional changes, and/or the frequency of the positional changes if the indicators are subjected to cyclic movements; and
  wherein the rule for mapping depends on the positional changes of the indicators and the maximum amplitude of the positional changes and/or the frequency of the positional changes.

\* \* \* \* \*

UNITED STATES PATENT AND TRADEMARK OFFICE
CERTIFICATE OF CORRECTION

PATENT NO. : 9,911,199 B2
APPLICATION NO. : 14/383121
DATED : March 6, 2018
INVENTOR(S) : Stefan Vilsmeier Page 1 of 1

It is certified that error appears in the above-identified patent and that said Letters Patent is hereby corrected as shown below:

In the Claims

Column 22, Line 25, phrase:
--more that--
Should read:
--more than--

Signed and Sealed this
Twenty-fourth Day of April, 2018

Andrei Iancu
*Director of the United States Patent and Trademark Office*